United States Patent
Callens et al.

(10) Patent No.: US 8,546,530 B2
(45) Date of Patent: Oct. 1, 2013

(54) PROCESS FOR THE MANUFACTURE OF PERSILYLATED PEPTIDES

(75) Inventors: Roland Callens, Grimbergen (BE); Thierry Delplanche, Mont-St-Guibert (BE)

(73) Assignee: Solvay (Societe Anonyme), Brussels (BE)

( * ) Notice: Subject to any disclaimer, the term of this patent is extended or adjusted under 35 U.S.C. 154(b) by 372 days.

(21) Appl. No.: 12/743,323

(22) PCT Filed: Nov. 18, 2008

(86) PCT No.: PCT/EP2008/065767
§ 371 (c)(1), (2), (4) Date: May 17, 2010

(87) PCT Pub. No.: WO2009/065836
PCT Pub. Date: May 28, 2009

(65) Prior Publication Data
US 2010/0298537 A1   Nov. 25, 2010

Related U.S. Application Data

(60) Provisional application No. 61/014,923, filed on Dec. 19, 2007.

(30) Foreign Application Priority Data

Nov. 19, 2007   (EP) .................................. 07121041

(51) Int. Cl.
| | |
|---|---|
| A61K 38/00 | (2006.01) |
| C07K 5/00 | (2006.01) |
| C07K 7/00 | (2006.01) |
| C07K 16/00 | (2006.01) |
| C07K 17/00 | (2006.01) |

(52) U.S. Cl.
USPC ........................................................ 530/333

(58) Field of Classification Search
None
See application file for complete search history.

(56) References Cited

U.S. PATENT DOCUMENTS

| | | | |
|---|---|---|---|
| 4,725,645 A | 2/1988 | Anteunis et al. | |
| 5,077,387 A | 12/1991 | Jacquier et al. | |
| 8,013,117 B2 * | 9/2011 | Kadzimirsz et al. | 530/328 |

FOREIGN PATENT DOCUMENTS

| | | |
|---|---|---|
| EP | 0184243 A1 | 6/1986 |
| EP | 0318338 A1 | 5/1989 |
| WO | WO 9005738 A1 | 5/1990 |
| WO | WO 9403494 A1 | 2/1994 |
| WO | WO 2004031215 A2 | 4/2004 |

OTHER PUBLICATIONS

Rabinovich et al. Use of the silylation reaction in synthesis of fragment 1-4 of the ACTH sequence. Translated from Khimiya Prirodnyk Soedinenii, 1988, Nol. 2, pp. 248-253.*
Pape. Silylating Agents. Kirk-Othmer Encyclopedia of Chemical Technology, Published online Jun. 16, 2006, vol. 22, pp. 1-15.*
Callens, "Cost-effective industry strategies for design,validation, production and purification: Peptisyntha 's method of producing GMP peptides on industrial Scale" International Business Communications 2nd International Conference on Peptide Technologies (1999)—conf 2317; 20 pgs.
Rogozhin et al.,"Synthesis of Tetrapedtide using Trimethylsilyl Amino Components", Isvestija Akademia Nauk SSSR, Seriya Khimicheskaya, No. 3. pp. 566-569 (1978); 4 pgs.
Kricheldorf, "Uber die Silylierung von Aminosauren und die Pepidsynthese mit Aminosauretrimethylsilylestern" Liebigs Ann. Chem. vol. 763, pp. 17-38 (1972); 12 pgs (in German).

* cited by examiner

*Primary Examiner* — Marcela M Cordero Garcia
(74) *Attorney, Agent, or Firm* — Mayer Brown LLP

(57) ABSTRACT

Process for the manufacture of a peptide or peptide analog, which comprises (a) producing a persilylated peptide or persilylated peptide analogue by silylating a corresponding peptide by reaction with a silylating agent other than trimethylsilylcyanide, and (b) reacting a compound of formula (I) X-A-COOH wherein X is an amino protecting group, A is an amino acid, peptide or peptide analogue residue, and —COOH designates an optionally activated carboxylic group, with a persilylated peptide or a persilylated peptide analogue containing from 4 to 15 amino acids.

12 Claims, No Drawings

PROCESS FOR THE MANUFACTURE OF PERSILYLATED PEPTIDES

CROSS-REFERENCE TO RELATED APPLICATIONS

The present patent application is a U.S. national stage application under 35 U.S.C. §371 of International Application No. PCT/EP2008/065767 filed Nov. 18, 2008, which claims priority benefit to U.S. provisional patent application No. 61/014,923 filed on Nov. 19, 2007 and to European patent application No. 07121041.3 filed on Nov. 19, 2007, the entire content of each application including its Sequence Listing being incorporated by reference into the present application for all purposes.

TECHNICAL FIELD OF THE INVENTION

The present invention relates to a process for the manufacture of peptides or peptide analogues making use of persilylation techniques.

BACKGROUND OF THE INVENTION

Peptides or peptide analogues are useful, for example as medicaments. One example of such peptide is Cetrorelix which can be used for the treatment of endometriosis and uterine fibroids in women, and benign prostatic hypertrophy in men. Cetrorelix is a gonadotrophin releasing hormone antagonist (GnRH antagonist) which has the following sequence.

```
                                             (SEQ ID NO: 1)
Ac-D-Nal-D-Cl-Phe-D-Pal-Ser-Tyr-D-Cit-Leu-Arg-Pro-
D-AlaNH2
```

Persilylation techniques are discussed in EP-A-184243, in Callens, IBC's $2^{nd}$ International Conference on Peptide Technologies, Rogozhin et al. Isvestija Akademia Nauk SSSR, Seriya Khimecheskaya, No. 3, p. 657-660 (1978) and Krich-eldorf, Liebigs Ann. Chem. 763, p. 17-38 (1972).

SUMMARY OF THE INVENTION

It has now been found a method for efficient and rapid peptide synthesis using persilylation technique which allows for good results in terms of productivity and purity of produced peptides or peptide analogues.

The invention concerns in consequence a process for the manufacture of a peptide or peptide analog, which comprises reacting a compound of formula (I) X-A-COOH wherein X is an amino protecting group, A is an amino acid, peptide or peptide analogue residue and —COOH designates an optionally activated carboxylic group, with a persilylated peptide or persilylated peptide analogue containing from 4 to 15 amino acids.

It has been found that preparative persilylation in large scale is possible for higher peptides such as tetrapeptides, pentapeptides etc. and that the latter have sufficient reactivity and solubility to allow for high yield manufacture of longer chain peptides and peptide analogues with high purity, in particular optical purity. It has also been found that silylating reagents other than trimethylcyanosilane are suitable for silylating longer chain peptides.

The invention further concerns a process for the manufacture of a peptide or peptide analog, which comprises (a) producing a persilylated peptide or persilylated peptide analogue by silylating a corresponding peptide by reaction with a silylating agent other than trimethylsilylcyanide and (b) reacting a compound of formula (I) X-A-COOH wherein X is an amino protecting group, A is an amino acid, peptide or peptide analogue residue and —COOH designates an optionally activated carboxylic group, with a persilylated peptide or a persilylated peptide analogue containing from 4 to 15 amino acids.

DETAILED DESCRIPTION OF THE PREFERRED EMBODIMENTS

In the present invention, "peptide" is understood to denote in particular a compound consisting essentially of amino acids bonded to each other through amide bonds.

In the present invention, "peptide analogue" is understood to denote in particular a compound consisting essentially of amino acids and optionally including other compounds which can be incorporated in a peptide, such as hetero substituted carboxylic acids e.g. hydroxy- or mercapto-carboxylic acid. Peptide analogues usually include at least 1 bond in the peptide sequence which is different from an amide bond, such as urethane, urea, ester or thioester bond.

Peptides or peptide analogues in the present invention can be linear, cyclic or branched and are preferably linear.

Amino acids which are useful as constituents of peptides or peptide analogues and residue "A" in the present invention include natural and non-natural amino acids. The amino acids can be selected, for example, from the following natural amino acids: Alanine, valine, norvaline, leucine, norleucine, isoleucine, serine, isoserine, homoserine, threonine, allothreonine, methionine, ethionine, glutamic acid, aspartic acid, asparagine, cysteine, cystine, phenylalanine, tyrosine, tryptophan, lysine, arginine, histidine, ornithine, glutamine and citrulline.

In particular, persilylated fragments containing serine, isoserine, homoserine and/or tyrosine, more particularly serine and/or tyrosine are preferred.

Unnatural enantiomers thereof can also be used.

The amino acids can be selected, for example, from the following amino acids of synthetic origin which: (1-naphthyl)alanine, (2-naphthyl)alanine, homophenylalanine, (4-chlorophenyl)alanine, (4-fluorophenyl)alanine, (3-pyridyl)alanine, phenylglycine, diaminopimelic acid (2,6-diaminoheptane-1,7-dioic acid), 2 aminobutyric acid, 2 aminotetralin-2-carboxylic acid, erythro-β-methylphenylalanine, β-methylphenylalanine, (2-methoxyphenyl)alanine, 1 amino-5-hydroxyindan-2-carboxylic acid, 2-aminoheptane-1,7-dioic acid, (2,6-dimethyl-4-hydroxyphenyl)alanine, erythro-β-methyltyrosine or threo-β-methyltyrosine.

The process steps of the process according to the invention are generally carried out in the liquid phase.

In the process according to the invention, the persilylated peptide contains preferably 4, 5, 6, 7, or 8 amino acids, more preferably 4, 5 or 6 amino acids. It is understood that these numbers apply analogously to the number of connected units in a peptide analogue.

Particular examples of peptide sequences which can suitably be reacted in persilylated form in the process according to the invention include:

H-Phe-Ile-Gly-Leu-OH (SEQ ID NO: 2)

H-Leu-Arg-Pro-(D)AlaNH2 (SEQ ID NO: 3)

H-Ser-Tyr-(D)Cit-Leu-Arg-Pro-(D)AlaNH2 (SEQ ID NO: 4)

H-Ser(tBu)-Thr-Cys(Trt)-Val-Leu-Gly-OH (SEQ ID NO: 5)

H-Trp-Ser-Tyr-(D)Ser(tBu)-Leu-Arg-Pro-NHNHCONH2 (SEQ ID NO: 6)

In step (a) of the process according to the invention, the persilylated peptide or peptide analogue is obtained by silylating a corresponding peptide (analogue) by reaction with a silylating agent, preferably in an organic solvent. The persilylated peptide or peptide analogue can be isolated and purified if desired. It is however preferred to use the persilylated peptide or peptide analogue in situ, e.g. by combining a solution containing persilylated peptide or peptide analogue with a solution containing, optionally activated, compound of formula (I).

In the present invention, it is preferred to use silylating agents not containing a cyano group such as N-trialkylsilyl amines or N-trialkylsilyl amides. Examples of such silylating reagents include N,O-bis(trimethylsilyl)acetamide, N,O-bis(trimethylsilyl)trifluoroacetamide, hexamethyldisilazane, N-methyl-N-trimethylsilylacetamide (MSA), N,-methyl-N-trimethylsilyltrifluoroacetamide, N-(trimethylsilyl)acetamide, N-(trimethylsilyl)diethylamine, N-(trimethylsilyl)dimethylamine, 1-(trimethylsilyl)imidazole, 3-(trimethylsilyl)-2-oxazolidone. N-methyl-N-trimethylsilylacetamide (MSA) is preferred.

hydrogen atom that react with the silylating agent such as amino, hydroxyl, mercapto or carboxyl groups.

It is understood that "persilylated" intends to denote in particular a peptide or a peptide analogue in which the groups having an active hydrogen atom that can react with the silylating agent are sufficiently silylated to ensure that a homogeneous reaction medium for coupling step (b) is obtained.

When the silylation is carried out in the presence of a solvent said solvent is preferably a polar organic solvent more preferably a polar aprotic organic solvent. An amide type solvent such as N,N-dimethylformamide or, in particular N,N-dimethylacetamide (DMAC) is more particularly preferred.

In another embodiment, silylation is carried out in a liquid silylation medium consisting essentially of silylating agent and peptide or peptide analogue.

In the present invention peptide or peptide analogue residue A is understood to denote in particular a peptide or peptide analogue which is bonded at its N-terminus or optionally corresponding position in a peptide analogue, to the carboxylic group of amino protected A comprises preferably from 2 to 20 amino acids and more preferably 2, 3, 4, 5, 6, 7, 8 or 9 amino acids.

Particular examples of sequences of compounds of formula A which can suitably reacted in the process according to the invention include:

Z-Asp(OtBu)-Ala-OH

Z-Ser-Tyr-(D)Cit-OH

Ac-(D)Nal-(D)Cph-(D)Pal-OH

Boc-Cys(Trt)-Ser(tBu)-Asn-Leu-OH (SEQ ID NO: 7)

Fmoc-His(Trt)-OH

The process according to the invention can be applied in particular to the following reactions:

| Product | Compound of formula (I) | Persilylated peptide or analog |
|---|---|---|
| Eledoïsin | Z-Asp(OtBu)-Ala-OH | H-Phe-Ile-Gly-Leu-OH (SEQ ID NO: 2) |
| Cetrorelix | Z-Ser-Tyr-(D)Cit-OH | H-Leu-Arg-Pro-(D)AlaNH$_2$ (SEQ ID NO: 3) |
| Cetrorelix | Ac-(D)Nal-(D)Cph-(D)Pal-OH | H-Ser-Tyr-(D)Cit-Leu-Arg-Pro-(D)AlaNH$_2$ (SEQ ID NO: 4) |
| Calcitonine | Boc-Cys(Trt)-Ser(tBu)-Asn-Leu-OH (SEQ ID NO: 7) | H-Ser(tBu)-Thr-Cys(Trt)-Val-Leu-Gly-OH (SEQ ID NO: 5) |
| Goserelin | Fmoc-His(Trt)-OH | H-Trp-Ser-Tyr-(D)Ser(tBu)-Leu-Arg-Pro-NHNHCONH$_2$ (SEQ ID NO: 6) |

The reaction of step (a) is generally carried out at a temperature from 0° C. to 100° C. preferably from 25° C. to 50° C.

In the reaction of step (a) generally 0.5 to 5 preferably 0.7 to 2 more preferably about 1 or 1 to 1.5 equivalent of silylating agent are used relative to the molar amount of functional groups to be silylated. Use of 2 to 4 equivalents of silylating agent relative to the molar amount of functional groups to be silylated is also possible. "Functional groups to be silylated" is understood to denote in particular groups having an active The term "amino protecting group X" refers to protecting groups which can be used to replace an acidic proton of an amino group in order to reduce its nucleophilicity. Typically, the amino protecting group X is removed in a deprotection reaction prior to the addition of the next amino acid to be added to the growing peptide chain. The amino protecting group X is preferably sterically hindering. The term "sterically hindering" is intended to denote in particular a substituent comprising at least 3 carbon atoms, in particular at least 4 carbon atoms, including at least one secondary, tertiary or quaternary carbon atom. The sterically hindering group often comprises at most 100, preferably at most 50 carbon atoms.

By way of non-limiting examples of amino protecting groups represented herein by X, mention may in particular be made of substituted or unsubstituted groups of acyl type, such as the formyl, acrylyl (Acr), benzoyl (Bz), acetyl (Ac), trifluoroacetyl, substituted or unsubstituted groups of aralkyloxycarbonyl type, such as the benzyloxycarbonyl (Z), p chlorobenzyloxycarbonyl, p bromobenzyloxycarbonyl, p nitrobenzyloxycarbonyl, p methoxybenzyloxycarbonyl, benzhydryloxycarbonyl, 2 (p biphenylyl)isopropyloxycarbonyl, 2 (3,5 dimethoxyphenyl)isopropyloxycarbonyl, p phenylazobenzyloxycarbonyl, triphenylphosphonoethyloxycarbonyl or 9 fluorenylmethyloxycarbonyl group (Fmoc), substituted or unsubstituted groups of alkyloxycarbonyl type, such as the tert-butyloxycarbonyl (BOC), tert-amyloxycarbonyl, diisopropylmethyloxycarbonyl, isopropyloxycarbonyl, ethyloxycarbonyl, allyloxycarbonyl, 2 methylsulphonylethyloxycarbonyl or 2,2,2 trichloroethyloxycarbonyl group, groups of cycloalkyloxycarbonyl type, such as the cyclopentyloxycarbonyl, cyclohexyloxycarbonyl, adamantyloxycarbonyl or isobornyloxycarbonyl group, and groups containing a hetero atom, such as the benzenesulphonyl, p toluenesulphonyl, mesitylenesulphonyl, methoxytrimethylphenylsulphonyl, 2-nitrobenzenesulfonyl, 2-nitrobenzenesulfenyl, 4-nitrobenzenesulfonyl or 4-nitrobenzenesulfenyl group. Among these groups X, those comprising a carbonyl, a sulfenyl or a sulphonyl group are preferred. An amino protecting group X is preferably selected from allyloxycarbonyl groups, tert-butyloxycarbonyl (BOC), benzyloxycarbonyl (Z), 9 fluorenylmethyloxycarbonyl (Fmoc), 4-nitrobenzenesulfonyl (Nosyl), 2-nitrobenzenesulfenyl (Nps) and substituted derivatives. More preferably, the amino protecting group X is tert-butyloxycarbonyl (BOC).

Amino protecting groups X may be introduced by various methods e.g. by reaction with suitable acid halides such as carbobenzoxyl chloride, or acid anhydrides such as acetic anhydride and di-tert-butyldicarbonate (BOC$_2$O). On the other hand, amino protecting groups X may be removed by acidolysis, hydrogenolysis, treatment with dilute ammonium hydroxide, treatment with sodium, treatment with sodium amide, treatment with hydrazine, or enzymatic hydrolysis. The process according to the invention often further comprises removing the group X from the compound produced by the reaction of the compound of formula (I) with the persilylated peptide.

In the process according to the invention, the reaction between the compound of formula (I) and the persilylated peptide is often carried out in the presence of a carboxyl group activating agent. In that case the carboxylic acid activating agent is suitably selected from carbodiimides, acyl halides, phosphonium salts and uronium or guanidinium salts. More preferably, the carboxylic acid activating agent is an acyl halide. Still more preferably, it is chosen from isobutyl chloroformate and pivaloyl chloride.

Good results are often obtained when using additional carboxylic activating reagents which reduce side reactions and/or increase reaction efficiency. For example, phosphonium and uronium salts can, in the presence of a tertiary base, for example, diisopropylethylamine (DIPEA) and triethylamine (TEA), convert protected amino acids into activated species (for example, BOP, PyBOP, HBTU, and TBTU all generate HOBt esters). Other reagents help prevent racemization by providing a protecting reagent. These reagents include carbodiimides (for example, DCC or WSCDI) with an added auxiliary nucleophile (for example, 1-hydroxy-benzotriazole (HOBt), 1-hydroxy-azabenzotriazole (HOAt), or HOSu) or derivatives thereof. Another reagent that can be utilized is TBTU. The mixed anhydride method, using isobutyl chloroformate, with or without an added auxiliary nucleophile, is also used, as is the azide method, due to the low racemization associated with it. These types of compounds can also increase the rate of carbodiimide-mediated couplings, as well as prevent dehydration of Asn and Gln residues. Typical additional reagents include also bases such as N,N-diisopropylethylamine (DIPEA), triethylamine (TEA) or N-methylmorpholine (NMM).

In the process according to the invention, the reaction of step (b) is generally carried out at a temperature from −50° C. to 50° C. preferably from −40° C. to 10° C.

In another aspect, the invention concerns the use of a polar organic solvent to provide a solution of a partially silylated peptide or peptide analogue obtained by reacting a compound of formula (I) X-A-COOH wherein X is an amino protecting group, A is an amino acid, peptide or peptide analogue residue and —COOH designates an optionally activated carboxylic group, with a persilylated peptide or a persilylated peptide analogue.

It has been found that it is possible to maintain in solution in a polar organic solvent partially silylated coupling products, in particular having at least 5 amino acids (or optionally analogous units), throughout the reaction to provide a homogeneous solution which is particularly suitable for work-up and purification or optional further reaction steps such as deprotection and subsequent coupling steps. Surprisingly, this is possible also when the reaction is carried out at low temperatures.

The polar organic solvent can be selected for example from ethers, in particular water-miscible ethers e.g. tetrahydrofurane, dioxane or 1,2-dimethoxyethane from nitroalkanes, in particular water-miscible nitroalkanes e.g. nitromethane or from amide-type solvents, in particular water-miscible amides.

In the use according to the invention, the polar organic solvent is preferably an amide type solvent, preferably selected from N,N-dimethylformamide and N,N-dimethylacetamide and N-methylpyrrolidone. More preferably the solvent is N,N-dimethylacetamide. This solvent allows for particularly efficient work-up and recovery of produced peptide or peptide analogue without substantial formation of by-products.

In the use according to the invention, the concentration of the partially silylated peptide or peptide analogue in the solution is generally equal to or greater than about 1% wt. relative to the total weight of the solution, preferably equal to or greater than about 5% wt. In the use according to the invention, the concentration of the partially silylated peptide or peptide analogue in the solution is generally equal to or less than about 20% wt. relative to the total weight of the solution, preferably equal to or less than about 15% wt.

In a particular aspect of the use according to the invention, the ratio of number of amino acid units and optional analogous units in A to the number of amino acid units and optional analogous units in the persilylated peptide or the persilylated peptide analogue is generally equal to or greater than 1:5 preferably equal to or greater than 1:4. In this aspect, said ratio to generally is equal to or lower than 3:2 preferably equal to or lower than 1:1.

In the use according to the invention, the solution contains generally from 10% wt. to 95% wt. of polar organic solvent relative to the total weight of the solution.

In the use according to the invention, the partially silylated peptide or peptide analogue is preferably obtained by the process according to the invention as described herein before.

In a particularly preferred embodiment of the use according to the invention, the solution is homogeneous at a temperature from −40° C. to +10° C.

The invention concerns also a process for the manufacture of a peptide or peptide analogue, comprising the use according to the invention.

The invention concerns also a solution comprising a peptide or peptide analogue containing from 4 to 15 amino acids in a liquid medium containing N-methyl-N-trimethylsilylacetamide and an amide type solvent. The amide type solvent is preferably N,N-dimethylacetamide.

EXAMPLES

The examples here after are intended to illustrate the invention without however limiting it.

In these examples and throughout this specification the abbreviations employed are defined as follows:

AcOH is acetic acid, AcOEt is ethyl acetate, Boc is t-butoxycarbonyl, n-BuOH is n-butanol, i-BuOH is iso-butanol, Cbz is benzyloxycarbonyl, DCC is 1,3 dicyclohexylcarbodiimide, DCM is dichloromethane, DIC is 1,3-diisopropylcarbodiimide, DIPEA is N,N-diisopropylethylamine, DMF is N,N-dimethylformamide, DMA is N,N-dimethylacetamide, EDC is 1-(3-Dimethylaminopropyl)-3-ethylcarbodiimide, Fmoc is fluorenylmethyloxycarbonyl, HBTU is N,N,N,N'-tetramethyl-O-(1H-benzotriazol-1-yl)uronium-hexafluororphosphate), HOBT is 1-hydroxybenzotriazole, HOOBT is 3,4-dihydro-3-hydroxy-4-oxo-1,2,3-benzotriazine, IBCF is isobutyl chloroformate, i-BuOH is isobutanol, IPE is diisopropylether, MeCN is acetonitrile, MeOH is methanol, MSA is N-Methyl-N-trimethylsilylacetamide, NMM is N-methylmorpholine, NMP is 1-methyl-2-pyrrolidone, tBu is tert. Butyl, TEA is triethylamine, THF is tetrahydrofuran, Tos is tosyl and Trt is trityl.

Example 1

[2+4]: Z-Asp(OtBu)-Ala-Phe-Ile-Gly-Leu-OH (SEQ ID NO: 8)

Under a nitrogen atmosphere, Phe-Ile-Gly-Leu (SEQ ID NO: 2) (1.0 eq) was dispersed in DCM and was dissolved at room temperature with MSA. Under a nitrogen atmosphere, Z-Asp(OtBut)-Ala (1.05 eq.) and TEA (1.0 eq.) were dissolved in a mixture of CH2Cl2/DMF at 25° C.±5 then cooled to −15° C. The carboxylic function was activated by the addition of Pyridine (1.0 eq) and pivaloyl chloride (1.0 eq). After 10 minutes, the silylated peptide was transferred on the activated peptide. The coupling reaction medium which was homogeneous was diluted with water leading to a two phase system. The CH2Cl2 was eliminated under vacuum whereby the peptide precipitated and Z-Asp(OtBut)-Ala-Phe-Ile-Gly-Leu was isolated by filtration, washed with water then dried under vacuum. We obtained a white solid with a yield of at least 70% in weight.

Example 2

(SEQ ID NO: 4)
[3 + 4]: Z-Ser-Tyr-(D)Cit-Leu-Arg-Pro-(D)AlaNH2.HCl

Under a nitrogen atmosphere, LeuArgPro(D)AlaNH2 (SEQ ID NO: 3) (1.05 eq) was dissolved in DMA and was silylated with MSA at maximum 40° C. then the solution was cooled to about −5° C. Under a nitrogen atmosphere, ZSerTyr(D)CitOH (1.0 eq) and HOOBt (1.05 eq) were dissolved in DMA at maximum 40° C. and the solution was cooled to about −5° C. Solution A was then transferred to solution B, the coupling was initiated by the addition of EDC.HCl (1.1 eq) and the reaction mixture was stirred at −5° C. for at least 1 hour then at about 5° C. during at least 3 hours. The end of the reaction was checked by HPLC. The solvent was removed under vacuum and the concentrate was then diluted in a 1% aqueous solution of NaCl and the pH was adjusted between 2.5 and 3.3 by the controlled addition of diluted HCl. In order to remove HOOBt and DMA, the aqueous solution was washed with DCM then the peptide was extracted three times with n-BuOH. The solvent was removed by evaporation under reduced pressure until water content was ≤1% weight. The slurry was progressively diluted with acetone by maintaining the temperature at about 45° C. to precipitate the peptide as a white solid which was filtered after stirring at about 20° C. during at least 1 hour. The solid was washed with acetone and finally with acetonitrile. The precipitate was dried until the acetone content was ≤2% weight and we obtained a white solid with a yield of at least 70% in weight.

Example 3

(SEQ ID NO: 1)
[3 + 7]: Ac-(D)Nal-(D)Cph-(D)Pal-Ser-Tyr-(D)Cit-Leu-Arg-Pro-(D)Ala-NH2.HCl

Under a nitrogen atmosphere, SerTyr(D)CitLeuArgPro(D)AlaNH2 (SEQ ID NO: 4) (1.05 eq) was dissolved in DMA and was silylated with MSA at maximum 40° C. for at least 60 minutes then the solution was cooled to about −5° C. Under a nitrogen atmosphere, Ac(D)NaI(D)Cph(D)PalOH (1.0 eq) and HOOBt (1.05 eq) are dissolved in DMA at maximum 40° C. and the solution was cooled to about −5° C. Solution A was then transferred to solution B, the coupling was initiated by the addition of EDC.HCl (1.1 eq) and the reaction mixture was stirred at −5° C. for at least 2 hours then at 5° C.±5 during at least 8 hours. The end of the reaction was checked by HPLC. The reaction mixture, which had remained homogenous throughout the reaction, was diluted with water and the pH was adjusted at 2.0±0.5 with a diluted aqueous solution of HCl. The solution was then washed twice with DCM at ±35° C. followed by triple extraction of the peptide with n-BuOH. The combined organic phases were finally washed with water. The solvent was removed by evaporation under reduced pressure until water content was ≤2% weight. The slurry was diluted with acetone to precipitate the peptide as a white solid which was filtered after stirring at about 15° C. during at least 1 hour. The solid was washed with acetone. The precipitate was dried until the acetone content was ≤5% weight. The dried solid was then triturated in a 1/1 mixture of MeOH and Acetone at about 20° C. during at least 1 hour,

Example 4

[4 + 7]: Boc-Cys(Trt)-Ser(tBu)-Asn-Leu-Ser(tBu)- (SEQ ID NO: 9)

Thr-Cys(Trt) Val Leu Gly OH

Under a nitrogen atmosphere, Ser(tBu)-Thr-Cys(Trt) Val Leu Gly OH (SEQ ID NO: 5) (1.0 eq) was dissolved in NMP and was silylated with MSA at maximum 50° C. for at least 90 minutes then the solution was cooled to about 5° C. Under a nitrogen atmosphere, Boc-Cys(Trt)-Ser(tBu)-Asn-Leu-OH (SEQ ID NO: 7) (1.02 eq) and NMM (1.05 eq.) were dissolved in NMP then the solution was cooled to −15° C.±5. The carboxylic moiety was then activated by the addition of IBCF (1.05 eq.). Solution A was then transferred to solution B and the reaction mixture was stirred at 0° C. for at least 60 minutes. The reaction mixture, which had remained homogenous throughout the reaction, was diluted with an aqueous solution of KHSO4 which precipitated the peptide. The solid was filtered, washed with water then with a 9/1 mixture of acetone and water. After drying, we obtained a white solid with a yield of at least 75% in weight.

Example 5

[4 + 7]: Fmoc-His(Trt)-Trp-Ser-Tyr-(D)Ser(tBu)- (SEQ ID NO: 10)

Leu-Arg-Pro-NHNHCONH2

Under a nitrogen atmosphere,

H-TrpSerTyr(D)Ser(tBu)LeuArgProNHNHCONH2

(SEQ ID NO: 6) (1.0 eq)

dissolved in DMA and was silylated with MSA at maximum 40° C. for at least 60 minutes. The solution was cooled to +25° C. and Fmoc-His(Trt)-OH (1.0 eq) and HBTU (1.1 eq.) are added, the solution was mixed at +25° C. until complete dissolution then was cooled to about −5° C. The coupling was initiated by the controlled addition of DIPEA (1.1 eq.). The end of the reaction was checked by HPLC. The reaction mixture, which had remained homogenous during the coupling, was diluted with an aqueous solution of KHSO4 which precipitated the peptide. The solid was filtered and washed with water. After drying, we obtained a white solid with a yield of at least 70% in weight.

---

The invention claimed is:

1. A process for the manufacture of a peptide or peptide analogue, which comprises (a) producing a persilylated peptide or persilylated peptide analogue containing from 4 to 15 amino acids by silylating a corresponding peptide by reaction with a silylating agent other than trimethylsilylcyanide; and (b) reacting a compound of formula (I) X-A-COOH, wherein X is an amino protecting group, A is an amino acid, peptide or peptide analogue residue, and —COOH designates an optionally activated carboxylic group, with the persilylated peptide or persilylated peptide analogue of step (a).

2. The process according to claim 1, wherein the persilylated peptide contains 4, 5, 6, 7, or 8 amino acids.

3. The process according to claim 1, wherein the reaction of step (a) is carried out in an organic solvent.

4. The process according to claim 1, wherein the silylating agent is N-methyl-N-trimethylsilylacetamide (MSA).

5. The process according to claim 3 wherein the organic solvent is N,N-dimethylacetamide (DMAC).

6. The process according to claim 1, wherein 0.7 to 1.5 equivalents of silylating agent are used relative to the molar amount of functional groups to be silylated.

7. The process according to claim 1, wherein A comprises 2, 3, 4, 5, 6, 7, 8 or 9 amino acids.

8. The process according to claim 1, wherein X is an electron-withdrawing amino protecting group.

9. The process according to claim 8, wherein X is a t-butoxycarbonyl group.

10. The process according to claim 1, wherein the reaction of step (b) is carried out in the presence of a carboxyl group activating agent selected from the group consisting of pivaloyl chloride and isobutyl chloroformate.

11. The process according to claim 1 further comprising removing the group X from the compound produced by the reaction.

12. The process according to claim 4, wherein the reaction of step (a) is carried out in an organic solvent which is N,N-dimethylacetamide (DMAC).

* * * * *

SEQUENCE LISTING

```
<160> NUMBER OF SEQ ID NOS: 10

<210> SEQ ID NO 1
<211> LENGTH: 10
<212> TYPE: PRT
<213> ORGANISM: artificial sequence
<220> FEATURE:
<223> OTHER INFORMATION: synthetic peptide
<220> FEATURE:
<221> NAME/KEY: VARIANT
<222> LOCATION: (1)..(1)
<223> OTHER INFORMATION: 3-(2-Naphthyl)-D-alanine
<220> FEATURE:
<221> NAME/KEY: VARIANT
<222> LOCATION: (2)..(2)
<223> OTHER INFORMATION: para-chloro-phenylalanine
<220> FEATURE:
<221> NAME/KEY: VARIANT
<222> LOCATION: (3)..(3)
<223> OTHER INFORMATION: 5-(3-pyridyl)-D-alanine
<220> FEATURE:
<221> NAME/KEY: VARIANT
<222> LOCATION: (6)..(6)
<223> OTHER INFORMATION: D-citrulline

<400> SEQUENCE: 1

Ala Phe Ala Ser Tyr Xaa Leu Arg Pro Ala
1               5                   10

<210> SEQ ID NO 2
<211> LENGTH: 4
<212> TYPE: PRT
<213> ORGANISM: artificial sequence
<220> FEATURE:
<223> OTHER INFORMATION: synthetic peptide
```

-continued

```
<400> SEQUENCE: 2

Phe Ile Gly Leu
1

<210> SEQ ID NO 3
<211> LENGTH: 4
<212> TYPE: PRT
<213> ORGANISM: artificial sequence
<220> FEATURE:
<223> OTHER INFORMATION: synthetic peptide
<220> FEATURE:
<221> NAME/KEY: VARIANT
<222> LOCATION: (4)..(4)
<223> OTHER INFORMATION: D-Alanine

<400> SEQUENCE: 3

Leu Arg Pro Ala
1

<210> SEQ ID NO 4
<211> LENGTH: 7
<212> TYPE: PRT
<213> ORGANISM: artificial sequence
<220> FEATURE:
<223> OTHER INFORMATION: synthetic peptide
<220> FEATURE:
<221> NAME/KEY: VARIANT
<222> LOCATION: (3)..(3)
<223> OTHER INFORMATION: D-citrulline
<220> FEATURE:
<221> NAME/KEY: VARIANT
<222> LOCATION: (7)..(7)
<223> OTHER INFORMATION: D-Alanine

<400> SEQUENCE: 4

Ser Tyr Xaa Leu Arg Pro Ala
1               5

<210> SEQ ID NO 5
<211> LENGTH: 6
<212> TYPE: PRT
<213> ORGANISM: artificial sequence
<220> FEATURE:
<223> OTHER INFORMATION: synthetic peptide
<220> FEATURE:
<221> NAME/KEY: VARIANT
<222> LOCATION: (1)..(1)
<223> OTHER INFORMATION: O-ter-butyl-serine
<220> FEATURE:
<221> NAME/KEY: VARIANT
<222> LOCATION: (3)..(3)
<223> OTHER INFORMATION: S-trityl-cysteine

<400> SEQUENCE: 5

Ser Thr Cys Val Leu Gly
1               5

<210> SEQ ID NO 6
<211> LENGTH: 7
<212> TYPE: PRT
<213> ORGANISM: artificial sequence
<220> FEATURE:
<223> OTHER INFORMATION: synthetic peptide
<220> FEATURE:
<221> NAME/KEY: VARIANT
<222> LOCATION: (4)..(4)
<223> OTHER INFORMATION: O-ter-butyl-D-serine

<400> SEQUENCE: 6

Trp Ser Tyr Ser Leu Arg Pro
1               5
```

```
<210> SEQ ID NO 7
<211> LENGTH: 4
<212> TYPE: PRT
<213> ORGANISM: artificial sequence
<220> FEATURE:
<223> OTHER INFORMATION: synthetic peptide
<220> FEATURE:
<221> NAME/KEY: VARIANT
<222> LOCATION: (1)..(1)
<223> OTHER INFORMATION: S-trityl-cysteine
<220> FEATURE:
<221> NAME/KEY: VARIANT
<222> LOCATION: (2)..(2)
<223> OTHER INFORMATION: O-ter-butyl-serine

<400> SEQUENCE: 7

Cys Ser Asn Leu
1

<210> SEQ ID NO 8
<211> LENGTH: 6
<212> TYPE: PRT
<213> ORGANISM: artificial sequence
<220> FEATURE:
<223> OTHER INFORMATION: synthetic peptide
<220> FEATURE:
<221> NAME/KEY: VARIANT
<222> LOCATION: (1)..(1)
<223> OTHER INFORMATION: aspartic acid beta-t-butyl

<400> SEQUENCE: 8

Asp Ala Phe Ile Gly Leu
1               5

<210> SEQ ID NO 9
<211> LENGTH: 10
<212> TYPE: PRT
<213> ORGANISM: artificial sequence
<220> FEATURE:
<223> OTHER INFORMATION: synthetic peptide
<220> FEATURE:
<221> NAME/KEY: VARIANT
<222> LOCATION: (1)..(1)
<223> OTHER INFORMATION: S-trityl-cysteine
<220> FEATURE:
<221> NAME/KEY: VARIANT
<222> LOCATION: (2)..(2)
<223> OTHER INFORMATION: O-ter-butyl-serine
<220> FEATURE:
<221> NAME/KEY: VARIANT
<222> LOCATION: (5)..(5)
<223> OTHER INFORMATION: O-ter-butyl-serine
<220> FEATURE:
<221> NAME/KEY: VARIANT
<222> LOCATION: (7)..(7)
<223> OTHER INFORMATION: S-trityl-cysteine

<400> SEQUENCE: 9

Cys Ser Asn Leu Ser Thr Cys Val Leu Gly
1               5                   10

<210> SEQ ID NO 10
<211> LENGTH: 8
<212> TYPE: PRT
<213> ORGANISM: artificial sequence
<220> FEATURE:
<223> OTHER INFORMATION: synthetic peptide
<220> FEATURE:
<221> NAME/KEY: VARIANT
<222> LOCATION: (1)..(1)
<223> OTHER INFORMATION: N-im-Trityl-histidine
<220> FEATURE:
```

```
<221> NAME/KEY: VARIANT
<222> LOCATION: (5)..(5)
<223> OTHER INFORMATION: O-ter-butyl-D-serine

<400> SEQUENCE: 10

His Trp Ser Tyr Ser Leu Arg Pro
1               5
```